United States Patent
Cherpeck et al.

(10) Patent No.: US 7,501,386 B2
(45) Date of Patent: Mar. 10, 2009

(54) SYNERGISTIC LUBRICATING OIL COMPOSITION CONTAINING A MIXTURE OF A BENZO[B]PERHYDROHETEROCYCLIC ARYLAMINE AND A DIARYLAMINE

(75) Inventors: Richard E. Cherpeck, Cotati, CA (US); Carrie Y. Chan, Daly City, CA (US)

(73) Assignee: Chevron Oronite Company, LLC, San Ramon, CA (US)

( * ) Notice: Subject to any disclaimer, the term of this patent is extended or adjusted under 35 U.S.C. 154(b) by 678 days.

(21) Appl. No.: 11/316,451

(22) Filed: Dec. 21, 2005

(65) Prior Publication Data

US 2007/0142243 A1   Jun. 21, 2007

(51) Int. Cl.
C07D 215/06 (2006.01)
C10M 133/40 (2006.01)

(52) U.S. Cl. ............. 508/269; 508/261; 546/165
(58) Field of Classification Search .......... 508/261, 508/269; 546/165
See application file for complete search history.

(56) References Cited

U.S. PATENT DOCUMENTS

| | | | |
|---|---|---|---|
| 1,896,461 A | 2/1933 | Muth | |
| 2,342,135 A | 2/1944 | Gibbs | |
| 2,718,501 A | 9/1955 | Harle | |
| 2,794,020 A | 5/1957 | Harris et al. | |
| 2,943,112 A | 6/1960 | Popoff et al. | |
| 2,958,663 A | 11/1960 | Westcott et al. | |
| 2,998,468 A | 8/1961 | Wilde | |
| 3,345,992 A | 10/1967 | Lederman et al. | |
| 3,362,929 A | 1/1968 | Kehe | |
| 3,452,056 A | 6/1969 | Sundholm | |
| 3,480,635 A | 11/1969 | Altwicker | |
| 3,505,225 A | 4/1970 | Wheeler | |
| 3,533,992 A | 10/1970 | Sundholm | |
| 3,655,559 A | 4/1972 | Holt | |
| 3,660,290 A | 5/1972 | Schlobohm | |
| 3,910,918 A | 10/1975 | Monroy | |
| 3,944,492 A | 3/1976 | Wheeler | |
| 4,069,195 A | 1/1978 | Layer et al. | |
| 4,089,792 A | 5/1978 | Lowe | |
| 4,692,258 A | 9/1987 | Rasberger et al. | |
| 4,965,006 A | 10/1990 | Meier et al. | |

(Continued)

FOREIGN PATENT DOCUMENTS

EP    0 022 281 B1    9/1983

(Continued)

OTHER PUBLICATIONS

McQueen, J.S. et al., Friction and wear of tribofilms formed by zinc dialkyl dithiophosphate antiwear additive in low viscosity engine oils, Elsevier Science Ltd., Tribology International 38, (2005), pp. 289-297.

(Continued)

*Primary Examiner*—Walter D Griffin
*Assistant Examiner*—Frank C Campanell
(74) *Attorney, Agent, or Firm*—Joseph P. Foley; Claude J. Caroli

(57) ABSTRACT

Disclosed is a lubricating oil composition containing an oil of lubricating viscosity and a particularly effective mixture of a benzo[b]perhydroheterocyclic arylamine and a diarylamine which together provide superior oxidation inhibition.

27 Claims, 1 Drawing Sheet

U.S. PATENT DOCUMENTS

| | | | |
|---|---|---|---|
| 5,198,134 | A | 3/1993 | Steinberg et al. |
| 5,232,614 | A | 8/1993 | Colclough et al. |
| 5,310,491 | A | 5/1994 | Downs et al. |
| 5,420,354 | A | 5/1995 | Malz et al. |
| 5,451,702 | A | 9/1995 | Stern et al. |
| 5,595,963 | A | 1/1997 | Puckace et al. |
| 5,834,544 | A | 11/1998 | Lin et al. |
| 6,121,209 | A | 9/2000 | Watts et al. |
| 6,174,842 | B1 | 1/2001 | Gatto et al. |
| 6,315,925 | B1 | 11/2001 | Aebli et al. |
| 6,426,324 | B1 | 7/2002 | Lai et al. |
| 6,806,241 | B2 | 10/2004 | Karol et al. |

FOREIGN PATENT DOCUMENTS

| | | |
|---|---|---|
| EP | 0 019 985 B1 | 11/1983 |

OTHER PUBLICATIONS

Ingold, K.U., Inhibition of the Autoxidation of Organic Substances in the Liquid Phase, Division of Applied Chemistry, National Research Council Publication No. 6537, American Chemical Society, Chemical Reviews, vol. 61, (1961), pp. 563-589.

Nishiyama, Tomihiro et al., Antioxidant activity of the fused heterocyclic compounds, 1,2,3,4-tetrahydroquinolines, and related compounds—effect of *ortho*-substituents, Elsevier Science Ltd., Polymer Degradation and Stability 79, (2003), pp. 225-230.

Dorey, Gilbert et al., New Quinolinic Derivatives as Centrally Active Antioxidants, Elsevier Science Ltd., Bioorganic & Medicinal Chemistry Letters 10, (2000), pp. 935-939.

Denisov, Evgeniy T. et al., Mechanisms of Action and Reactivities of the Free Radicals of inhibitors, American Chemical Society, Chemical Reviews, vol. 87, No. 6 (1987), pp. 1313-1357.

Nishiyama, Tomihiro et al., Antioxidant activity of aromatic cyclic amine derivatives, Elsevier Science Ltd., Polymer Degradation and Stability 75, (2002), pp. 549-554.

SYNERGISTIC LUBRICATING OIL COMPOSITION CONTAINING A MIXTURE OF A BENZO[B]PERHYDROHETEROCYCLIC ARYLAMINE AND A DIARYLAMINE

FIELD OF THE INVENTION

The present invention is directed in part to a lubricating oil composition containing an oil of lubricating viscosity and a particularly effective mixture of a benzo[b]perhydroheterocyclic arylamine and a diarylamine which together provide superior oxidation inhibition.

BACKGROUND OF THE INVENTION

Diarylamine antioxidants are known and have been widely used to improve the thermal-oxidative stability and/or light induced degradation in numerous products used in engineering; for example, they can improve the performance properties in lubricants, hydraulic fluids, metal working fluids, fuels or polymers, just to name a few.

Commonly, these diarylamines have been alkylated, see for example, U.S. Pat. No. 2,943,112 which discloses an improved process for alkylating diphenylamine and U.S. Pat. No. 3,655,559 which discloses alkylated diphenylamines as stabilizers. Alkaryl substituted diphenylamines and phenyl-napthylamines (such as α-methylstyryl-diphenylamine) are disclosed for example in U.S. Pat. Nos. 3,533,992; 3,452,056 and 3,660,290.

Additionally, alkyl substituted 1,2-dihydroquinoline and polymers thereof, have been employed as antioxidants, see U.S. Pat. No. 3,910,918. While, U.S. Pat. No. 5,310,491 discloses the reaction product of an alkyl substituted 1,2-dihydroquinoline with a diarylamine. Tetrahydroquinones and substituted tetrahydroquinones have also have also been disclosed as antioxidants, see for example U.S. Pat. Nos. 2,794,020; 3,362,929; 4,692,258 and 4,965,006. Likewise decahydroquinolines and substituted decahydroquinolines have been employed as antioxidants, see U.S. Pat. Nos. 2,998, 468 and 4,069,195.

Synergist and antagonist combinations of antioxidants have been disclosed. Effective synergistic mixtures of antioxidants are typically compounds that intercept oxidation by two different mechanisms. For example, those in which one compounds functions as decomposer of peroxides and the other compound functions as an inhibitor of free radicals. Well known heterosynergism has been disclosed between sulfur and phosphorous containing compounds (such as sulfides, dithiocarbamates, phosphites and dithiophosphates) and aminic or phenolic antioxidants. U.S. Pat. No. 2,718,501 discloses a synergistic mixture of a sulfur-containing compound, such as a wax sulfide or dioctadecyl disulfide, and an aromatic amine compound having at least 2 aromatic rings, such as phenyl alpha-naphthyl amine, for use in preventing oxidation in lubricating oils. For example, U.S. Pat. No. 2,958,663 discloses an extreme pressure lubricant composition containing from 0.01 to 5 percent each of sulfurized oleic acid, $C_{18}$-$C_{22}$ alkenyl succinic acid, chlorinated paraffin wax containing from 20 to 60 percent chlorine, diphenylamine and N,N-salicylal-1,2-propylenediamine. U.S. Pat. No. 3,345,292 discloses stabilized alkyl substituted diaryl sulfides for use as functional fluids where the stabilizer can be diaryl amine or alkylated phenol. U.S. Pat. No. 4,089,792 discloses lubricants having a an antioxidant mixture of a primary amine and an antioxidant selected from aromatic or alkyl sulfides and polysulfides, sulfurized olefins, sulfurized carboxylic acid esters and sulfurized ester-olefins. This composition may also contain zinc dialkyldithiophosphates.

SUMMARY OF THE INVENTION

The present is directed in part to a lubricating oil composition which provides improved oxidation stability. According the compositions of the present invention have various uses such as lubricants for automotive and truck crankcase lubricants; as well as transmission lubricants, gear lubricants, hydraulic fluids, compressor oils, diesel and marine lubricants. The lubricating oil compositions of the present invention comprise a lubricating oil and a synergistic mixture of antioxidants, said mixture containing a) from 0.1 to 10 weight percent of a first antioxidant according to formula I:

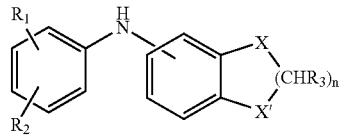

Formula I wherein
$R_1$ and $R_2$ are each independently selected from the group consisting of hydrogen, alkyl from 1 to 20 carbon atoms, —OR, —SR and —NRR', where R and R' are independently hydrogen or alkyl from 1 to 6 carbon atoms, or $R_1$ and $R_2$ when adjacent to each other together form a 5 to 6 membered alicyclic or aromatic ring which may be optionally substituted with 1 or 2 alkyl groups each having from 1 to 20 carbon atoms;
each $R_3$ is hydrogen or alkyl from 1 to 6 carbon atoms,
X and X' are independently selected from —$CHR_4$—, oxygen, sulfur or $NR_5$, wherein $R_4$ and $R_5$ are independently hydrogen or alkyl from 1 to 6 carbon atoms, with the proviso that at least one of X or X' is a heteroatom positioned ortho or para to the bridging nitrogen atom, and when X or X' are nitrogen then $R_1$ or $R_2$ is not hydroxyl; and further provided that when one of X or X' is —$CHR_4$— then the other may not be oxygen; and
n is an integer from 1 to 2; and
b) from 0.01 to 10 weight percent of a second antioxidant selected from the formula

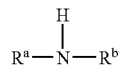

wherein $R^a$ and $R^b$ are each independently aryl from 6 to 10 carbon atoms which may be unsubstituted or substituted with one or two alkyl groups each having from 1 to 20 carbon atoms.

Dramatic improvement of the combination of component a) and component b) is demonstrated at ratios of component a) to component b) from about 0.5:1 to about 10:1 and even more particularly from about 0.75:1 to about 5.1. Due to the dramatic improvement in oxidative stability of the composition afforded by the mixture of components a) & b), the mixture of these components present in the total composition is less than 5 weight percent. More preferably the mixture of a) & b) is from 0.5 to 2.0 weight percent based on the total weight of the composition.

The benzo[b]perhydroheterocycle of component a) can contain one or two heteroatoms and preferably contains at least one nitrogen or oxygen atom, with nitrogen being particularly preferred, thus in this aspect at least one X or X' is oxygen of $NR_5$, with —NH— being particularly preferred. The single nitrogen benzo[b]perhydroheterocycle can be characterized as having being unsubstituted on the heterocyclic ring but, optionally substituted on the aryl ring, thus $R_1$ and $R_2$ are each independently selected from the group consisting of hydrogen, alkyl from 1 to 20 carbon atoms, —OR, —SR and —NRR', where R and R' are independently hydrogen or alkyl from 1 to 6 carbon atoms, or $R_1$ and $R_2$ when adjacent to each other together form a 5 to 6 membered alicyclic or aromatic ring which may be optionally substituted with 1 or 2 alkyl groups each having from 1 to 20 carbon atoms, and more particularly wherein $R_1$ and $R_2$ are each independently selected from the group consisting of hydrogen and alkyl from 1 to 20 carbon atoms.

In yet another aspect, X and X' are independently selected from oxygen, sulfur or $NR_5$, wherein $R_5$ is hydrogen or alkyl from 1 to 6 carbon atoms. Thus, both X and X' can be oxygen or for example, nitrogen.

In the compounds of formula I, $R_1$ and $R_2$ together with the atoms between them, can form alicyclic or aromatic ring. Thus, one aspect of the compound is directed to when $R_1$ and $R_2$ are adjacent to each other and together form a 5 to 6 membered aromatic ring which may be optionally substituted with 1 or 2 alkyl groups each having from 1 to 20 carbon atoms. Other aspects are characterized for example, wherein $R_1$ is hydrogen and $R_2$ is selected from the group consisting of alkyl from 1 to 20 carbon atoms, —OR, —SR and —NRR', where R and R' are independently hydrogen or alkyl from 1 to 6 carbon atoms, with the tertiary amines being preferred.

The composition defined above can contain other additives. Thus another aspect of the present invention further comprises component c) an oil soluble molybdenum compound. A particularly preferred oil soluble molybdenum compound is an unsulfurized or sulfurized oxymolybdenum containing composition prepared by (i) reacting an acidic molybdenum compound and a basic nitrogen compound selected from the dispersant group consisting of succinimide, a carboxylic acid amide, a hydrocarbyl monoamine, a phosphoramide, a thiophosphoramide, a Mannich base, a dispersant viscosity index improver, or a mixture thereof in the presence of a polar promoter, to form an oxymolybdenum complex. More preferably the basic nitrogen compound is a succinimide.

The composition above can further comprise an oil-soluble, phosphorus-containing, anti-wear compound selected from the group consisting of metal dithiophosphates, phosphorus esters, amine phosphates and amine phosphinates, sulfur-containing phosphorus esters, phosphoramides and phosphonamides. Preferred said phosphorus esters are selected from the group consisting of phosphates, phosphonates, phosphinates, phosphine oxides, phosphites, phosphonites, phosphinites, and phosphines. Particularly preferred oil-soluble, phosphorus-containing, anti-wear compound is a metal dithiophosphate, such as zinc dialkyldithiophosphate.

The composition above can contain an oil soluble decomposer of peroxides.

DETAILED DESCRIPTION OF THE INVENTION

Figure 1:
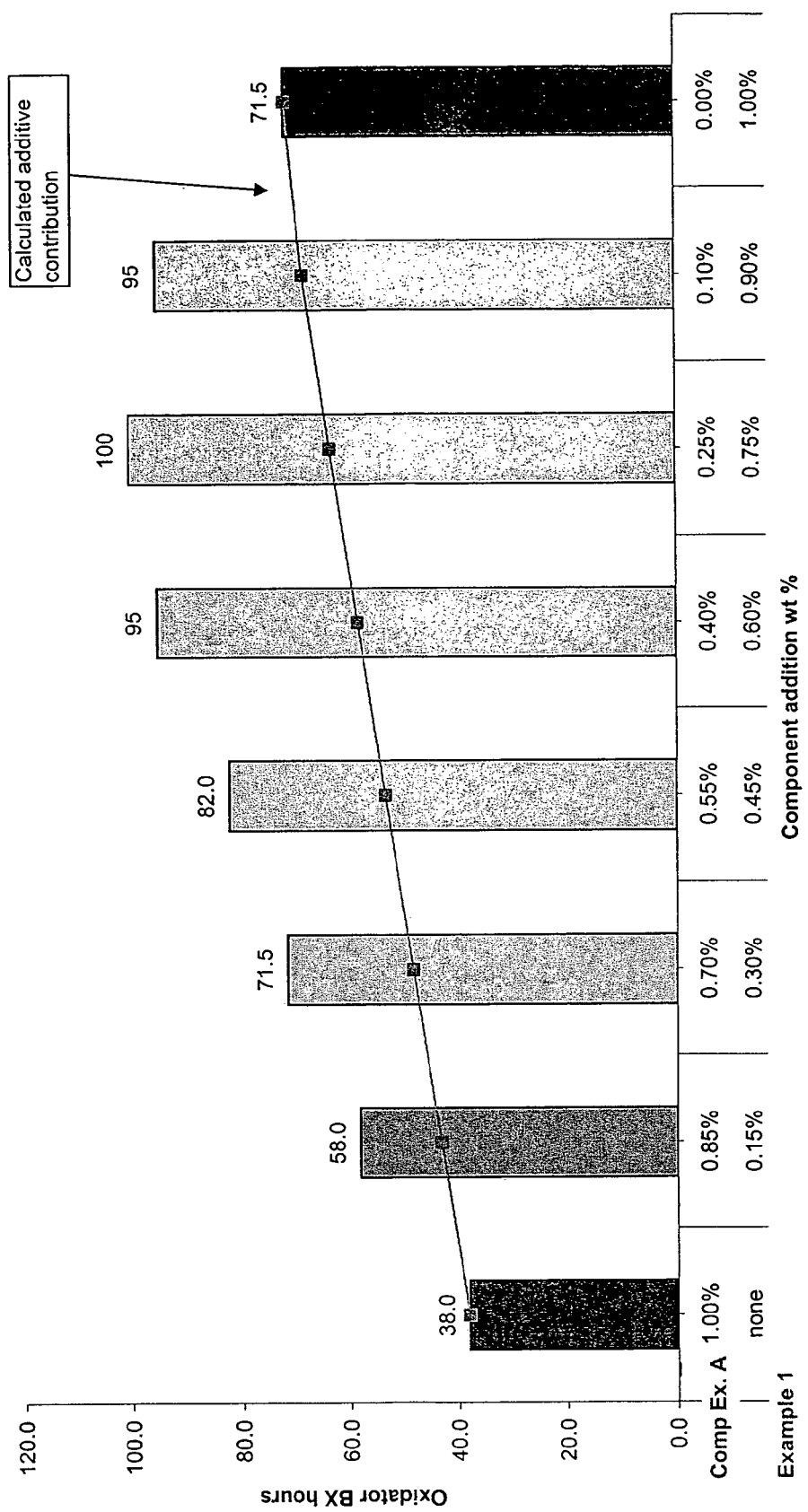
FIG. 1 is a graph of the oxidation inhibition of the mixtures of component a) and component b) of the present invention. The line graph is representative of the calculated additive contribution of the components.

Inhibition of free radical-mediated oxidation is one of the most important reactions in organic substrates and is commonly used in rubbers, polymers and lubrication oils; namely, since these chemical products may undergo oxidative damage by the autoxidation process. Hydrocarbon oxidation is a three step process which comprises: initiation, propagation and termination. Oxidative degradation and the reaction mechanisms are dependent upon the specific hydrocarbons, temperatures, operating conditions, catalysts such as metals, etc., which more detail can be found in Chapter 4 of Mortier R. M. et al., 1992, "Chemistry and Technology of Lubricants Initiation", VCH Publishers, Inc.; incorporated herein by reference in its entirety. Initiation involves the reaction of oxygen or nitrogen oxides ($NO_x$) on a hydrocarbon molecule. Typically, initiation starts by the abstraction of hydrocarbon proton. This may result in the formation of hydrogen peroxide (HOOH) and radicals such as alkyl radicals (R.) and peroxy radicals (ROO.). During the propagation stage, hydroperoxides may decompose, either on their own or in the presence of catalysts such as metal ions, to alkoxy radicals (RO.) and peroxy radicals. These radicals can react with the hydrocarbons to form a variety of additional radicals and reactive oxygen containing compounds such as alcohols, aldehydes, ketones and carboxylic acids; which again can further polymerize or continue chain propagation. Termination results from the self termination of radicals or by reacting with oxidation inhibitors.

The uncatalyzed oxidation of hydrocarbons at temperatures of up to about 120° C. primarily leads to alkyl-hydroperoxides, dialkylperoxides, alcohols, ketones; as well as the products which result from cleavage of dihydroperoxides such as diketones, keto-aldehydes hydroxyketones and so forth. At higher temperatures (above 120° C.) the reaction rates are increased and cleavage of the hydroperoxides plays a more important role. Additionally, at the higher temperatures, the viscosity of the bulk medium increases as a result of the polycondesation of the difunctional oxgenated products formed in the primary oxidation phase. Further polycondesation and polymerization reaction of these high molecular weight intermediates results in products which are no longer soluble in the hydrocarbon and form varnish like deposits and sludge.

Since autoxidation is a free-radical chain reaction, it therefore, can be inhibited at the initiation and/or propagation steps. Typical oxidation inhibition by diarylamines, such as dialkyldiphenylamine and N-phenyl-α-napthylamine, also involves radical scavenging. The transfer of hydrogen from the NH group of the amine to the peroxide radicals results in the formation of a diarylamino radical which is resonance stabilized, thus prevents new chains from forming. A secondary peroxy radical or hydroperoxide can react with the diarylamino radical to form the nitroxy radical, which is also a very potent inhibitor. Increased demands have been placed on many functional fluids which have in-turn placed emphasis on new inhibitors.

The present invention is directed in part to a mixture of compounds which imparts a synergistic antioxidant effect in a hydrocarbon. The first component a) is aryl-amino bridged benzo[b]perhydroheterocyclic compound which alone is particularly useful as a stabilizer; however in addition with component b) a secondary aryl amine, the combination has improved oxidation stability. Synergism has been suggested for combinations of different types of antioxidants also called heterosynergism due to the different mechanism of stabilizer, for example a combination of radical scavengers and peroxide decomposers. Additionally, it has been suggested even within the same class, compounds which act by a different reaction mechanism/rate may lead to synergist results, for example combinations of hindered phenolics and alkylated diphenylamines has been studied. Heretofore, synergism has not demonstrated for a mixture of a) aryl-amino bridged benzo[b]perhydroheterocyclic compound and b) a secondary aryl amine.

Benzo[b]Perhydrohetocyclic Arylamine—Component a)

Component a) is a benzo[b]perhydrohetocyclic arylamine which alone may serve as an antioxidant, antiozoant, heat stabilizer and ultraviolet light stabilizer and these compounds are oil soluble, thus particularly suited for use an antioxidant in a lubricating oil composition. Disclosed are particularly suited resonance stabilized inhibitor compounds according to formula I:

Formula I

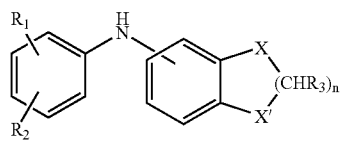

wherein: $R_1$ and $R_2$ are independently selected from the group consisting of hydrogen, alkyl from 1 to 20 carbon atoms, —OR, —SR and —NRR', where R and R' are independently hydrogen or alkyl from 1 to 6 carbon atoms, or $R_1$ and $R_2$ when adjacent to each other together from a 5 to 6 member ring, said ring is selected from a 5 to 6 membered alicyclic ring and a 5 to 6 membered aromatic ring, wherein said ring may be unsubstituted or substituted with 1 or 2 alkyl groups each having from 1 to 20 carbon atoms; each $R_3$ is hydrogen or alkyl from 1 to 6 carbon atoms, X and X' are independently selected from —$CHR_4$—, oxygen, sulfur or $NR_5$, wherein $R_4$ and $R_5$ are independently hydrogen or alkyl from 1 to 6 carbon atoms, with the proviso that at least one of X or X' is a heteroatom positioned ortho or para to the bridging nitrogen atom, and further provided that when one of X or X' is —$CHR_4$— then the other may not be oxygen, and when X or X' are nitrogen then $R_1$ or $R_2$ is not hydroxyl; and n is an integer from 1 to 2. Nitrogen is a particularly preferred heteroatom, which is more preferred than oxygen, which both are more preferred than sulfur. Improved resonance stabilization may be accomplished by substituents on the rings, thus particularly preferred groups are electron donating groups, more so when positioned ortho and para positions to the bridging nitrogen atom, thereby stabilizing this amino radical. Therefore, preferably at least one $R_1$ and $R_2$ is —OR, —SR or —NRR' with —NRR' being preferred. In another aspect, there is only a single substituent on the aryl group, thus $R_1$ is hydrogen with $R_2$ selected from —OR, —SR or —NRR' with —NRR' being preferred; wherein R and R' are defined herein above and even more preferred, R is alkyl from 1 to 6 carbon atoms.

By way of an example, when X is selected to be the heteroatom, the ortho and para positions of X to the bridging nitrogen atom are depicted below.

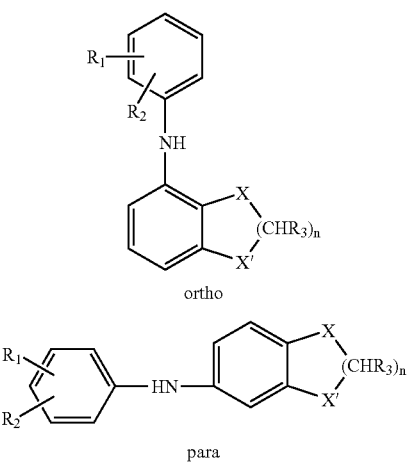

The requirement for the ortho and para position are more prevalent when X' is —$CHR_4$— which is a preferred embodiment. Additionally, $R_1$ and $R_2$, when other than hydrogen, are preferably positioned so that at least one is in the ortho orpara position to the bridging nitrogen atom.

In one preferred aspect, $R_1$ is hydrogen and $R_2$ is selected from the group consisting of alkyl from 1 to 20 carbon atoms, —OR, —SR and —NRR', where R and R' are independently hydrogen or alkyl from 1 to 6 carbon atoms; also preferred in the above, is where R is alkyl from 1 to 6. Preferably in the above, $R_2$ is positioned in the ortho orpara position to the bridging nitrogen atom. Alkyl chains have demonstrated improved oil solubility in the resulting compound, therefore straight and branched chain alkyl from 3 to 18 carbon atoms are particularly preferred when the compounds are employed in lubricating oil compositions. Nitrogen and oxygen heterocycles have demonstrated robust properties and thus, preferably at least one X or X' contains a nitrogen or oxygen atom, with nitrogen being particularly preferred, with single nitrogen atom heterocycles even more preferred.

In another preferred aspect, $R_1$ and $R_2$ are each independently selected from the group consisting of alkyl from 1 to 20 carbon atoms, —OR, —SR and —NRR', where R is alkyl from 1 to 6 carbon atoms and R' is hydrogen or alkyl from 1 to 6 carbon atoms. In another aspect, when $R_1$ and $R_2$ are located on adjacent carbon atoms, $R_1$ and $R_2$ together can form a 5 to 6 membered alicyclic or aromatic ring which may be unsubstituted or substituted with 1 or 2 alkyl groups each having from 1 to 20 carbon atoms, preferably alkyl from 3 to 18 carbon atoms. Preferably at least one X or X' contains a nitrogen or oxygen atom, with nitrogen being particularly preferred, with single nitrogen atom heterocycles even more preferred.

In formula I, particularly preferred compounds are depicted when at least one X and X' is selected from nitrogen or oxygen and even more preferred is when at least one X and X' is nitrogen. These nitrogen containing perhydroheterocycle compounds are further defined according to formula II Accordingly, particularly preferred compounds are depicted by the formula

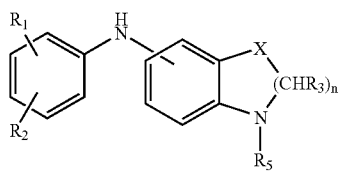

Formula II wherein $R_1$, $R_2$, $R_3$, $R_5$, X and n, are defined herein above, with the proviso the heterocyclic nitrogen is positioned ortho or para to the bridging nitrogen atom and further providing that when X is —$CHR_4$— then $R_1$ and $R_2$ are not hydroxyl. As stated above, alkyl substituents have been employed to improve oil solubility and are particularly useful when there is greater than two heteroatoms in the compound. Preferably, if the compound is to contain alkyl groups, the alkyl groups are characterized in regard with $R_1$ or $R_2$. Thus preferably at least one $R_1$ and $R_2$ are alkyl from 1 to 20 carbon atoms, or —OR, —SR and —NRR', where R is alkyl from 1 to 6 carbon atoms and R' is defined above. Additionally, $R_1$ and $R_2$ when adjacent to each other together can form a 5 to 6 membered alicyclic or aromatic ring which is substituted with 1 or 2 alkyl groups each having from 1 to 20 carbon atoms. Even more preferred is that $R_3$ and $R_4$ are hydrogen.

Particularly preferred compounds of Formula II are depicted when n is equal to two. Even more preferred are the tetrahydro-quinolines, thus X is —$CHR_4$— and the bridging ring nitrogen is attached at the 6 or 8 position.

In formula I, when n=1, the compounds can be depicted by formula Ia

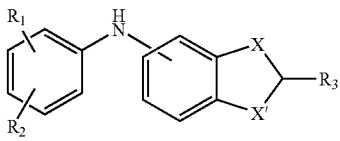

Formula Ia wherein: $R_1$ and $R_2$ are each independently selected from the group consisting of hydrogen, alkyl from 1 to 20 carbon atoms, —OR, —SR and —NRR', where R and R' are independently hydrogen or alkyl from 1 to 6 carbon atoms, or $R_1$ and $R_2$ when adjacent to each other together form a 5 or 6 membered alicyclic or aromatic ring which may be unsubstituted or substituted with 1 or 2 alkyl groups each having from 1 to 20 carbon atoms; $R_3$ is hydrogen or alkyl from 1 to 6 carbon atoms; X is oxygen, sulfur, —NH— or —N(alk)- where alk is alkyl from 1 to 6 carbon atoms with the proviso that the X heteroatom is positioned ortho or para to the bridging nitrogen atom; X' is selected from —$CHR_4$—, oxygen, sulfur or $NR_5$, wherein $R_4$ and $R_5$ are independently hydrogen or alkyl from 1 to 6 carbon atoms, with the proviso that when X is oxygen then X' is oxygen, sulfur or $NR_5$. Particularly suited fused ring perhydroheterocylic moieties include substituted and unsubstituted: 2,3-dihydro-indole, 2,3-dihydro-benzo[b]thiophene, 2,3-dihydro-benzoimidazole including alkyl and dialkyl substituted dihydro-benzoimidazoles, 2,3dihydro-benzooxaole, 2,3-dihydro-benzothiazole, benzo[1,3]dithiole, benzo[1,3]oxathiole and benzo[1,3]dioxole.

In formula I, when n=2, particularly useful heterocyclic rings are selected from substituted and unsubstituted heterocyclic rings consisting of the group: 1,2,3,4-tetrahydroquinoline; 1,2,3,4-tetrahydroqinoxaline; 3,4-dihydro-2H-benzo[1,4]thiazine; 3,4-dihydro-2H-benzo[1,4]oxazine; thiochroman, 2,3-dihydro-benzo[1,4]dithiine; 2,3-dihydro-benzo[1,4]oxathiine; 2,3-dihydro-benzo[1,4]dioxine and chroman.

The compounds of formula I are particularly useful when employed in a lubricating composition comprising the compound of formula I with an oil of lubricating viscosity. The concentration of the compound of formula I in the lubricating composition can vary depending upon the requirements, applications and degree of synergy desired. In a preferred embodiment of the invention, a practical benzo[b]perhydroheterocyclic arylamine use range in the lubricating composition is from about 1,000 parts per million to 20,000 parts per million (i.e. 0.1 to 2.0 wt %) based on the total weight of the lubricating oil composition, preferably the concentration is from 1,000 to 10,000 parts per million (ppm) and more preferably from about 2,000 to 8,000 ppm by weight.

Diarylamine—Component b):

The secondary diarylamines are well known antioxidants. Preferably, the secondary diarylamine antioxidant is one of the formula $R^a$—NH—$R^b$, wherein $R^a$ and $R^b$ each independently represent a substituted or unsubstituted aryl group having from $C_6$ to $C_{30}$ carbon atoms, preferably $R^a$ and $R^b$ are each independently aryl from 6 to 10 carbon atoms which may be unsubstituted or substituted with one or two alkyl groups each having from 1 to 20 carbon atoms.

Illustrative of substituents for the aryl moieties are aliphatic hydrocarbon groups, such as alkyl or alkenyl of 1 to 20 carbon atoms. The aryl moieties are preferably substituted or unsubstituted phenyl or substituted or unsubstituted naphthyl, particularly where one or both of the aryl moieties are substituted with alkyl, such as one having 4 to 18 carbon atoms.

The aliphatic hydrocarbon moiety, which can be of 1 to 20 carbon atoms, can have either a straight chain or a branched chain, which may be a fully saturated or a partially unsaturated hydrocarbon chain; for example, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, oleyl, nonadecyl, and the like, and isomers and mixtures thereof.

Preferably either $R^a$ and/or $R^b$ contain substituted aryl groups. These secondary diarylamines may be unsubstitited or substituted at one or both rings with alkyl groups, preferably straight and branched alkyl groups from 4 to 12 carbon atoms, more preferably 8 to 9 carbon atoms. Commonly mixtures of alkylated diphenylamines are prepared such as that prepared by reacting diphenylamine with 2,4,4-trimethylpentyl; or employing other alkyl groups, preferably branched chain to prepare for example nonylated diphenylamine (bis(4-nonylphenyl)amine) or octylated-butylated diphenyl amine.

For exhibiting good solubility of their oxidized product in base oil, these $C_{20}$ or less alkyl groups are preferably $C_{8-16}$ branched alkyl groups, more preferably those $C_{8-6}$ branched alkyl groups derived from oligomers of $C_3$ or $C_4$ olefins. The $C_3$ or $C_4$ olefins referred to here include propylene, 1-butene, 2-butene and isobutylene, among which propylene and isobutylene are preferable for good solubility of their oxidized product in base oil. Specifically, a branched octyl group derived from an isobutylene dimer, a branched nonyl group derived from a propylene trimer, a branched dodecyl group derived from an isobutylene trimer, a branched dodecyl group derived from a propylene tetramer or a branched pentadecyl group derived from a propylene pentamer is particularly preferable. The substituted secondary diaryl amines and particualry p,p'-dialkyl diphenyl amines and N-p-alkylphenyl-α-naphthyl amines, may be a commercially available product, but can be easily produced by reacting the diaryl amine with a $C_{1-6}$ alkyl halide, a $C_{2-6}$ olefin, or a $C_{2-6}$ olefin oligomer with secondary diaryl amine by use of a Friedel-Crafts catalyst. Examples of the Friedel-Crafts catalyst are metal halides such as aluminum chloride, zinc chloride and iron chloride, and acidic catalysts such as sulfuric acid, phosphoric acid, phosphorus pentoxide, boron fluoride, acidic clay and active clay. Other alkylation methods are known in the art.

Examples of some of the secondary diarylamines that are useful in the practice of the present invention include: diphenylamine, monoalkylated diphenylamine, dialkylated diphenylamine, trialkylated diphenylamine, or mixtures thereof, mono- and/or di-butyldiphenylamine, mono- and/or di-octyldiphenylamine, mono- and/or di-nonyldiphenylamine, phenyl-alpha-naphthylamine, phenyl-beta-naphthylamine, diheptyldiphenylamine, t-octylated N-phenyl-1-naphthylamine, mixtures of mono- and dialkylated t-butyl-t-octyl-diphenylamine.

Examples of commercial diarylamines include, for example, IRGANOX L06, IRGANOX L57 and IRGANOX L67 from Ciba Specialty Chemicals; NAUGALUBE AMS, NAUGALUBE 438, NAUGALUBE 438R, NAUGALUBE 438L, NAUGALUBE 500, NAUGALUBE 640, NAUGALUBE 680, and NAUGARD PANA from Crompton Corporation; GOODRITE 3123, GOODRITE 3190X36, GOODRITE 3127, GOODRITE 3128, GOODRITE 3185X1, GOODRITE 3190X29, GOODRITE 3190X40, GOODRITE 3191 and GOODRITE 3192 from BF Goodrich Specialty Chemicals; VANLUBE DND, VANLUBE NA, VANLUBE PNA, VANLUBE SL, VANLUBE SLHP, VANLUBE SS, VANLUBE 81, VANLUBE 848, and VANLUBE 849 from R. T. Vanderbilt Company Inc.

The concentration of the secondary diarylamine in the lubricating composition can vary depending upon the requirements, applications and degree of synergy desired. In a preferred embodiment of the invention, a practical secondary diarylamine use range in the lubricating composition is from about 1,000 parts per million to 20,000 parts per million (i.e. 0.1 to 2.0 wt %) based on the total weight of the lubricating oil composition, preferably the concentration is from 1,000 to 10,000 parts per million (ppm) and more preferably from about 2,000 to 8,000 ppm by weight.

Typically, with regard to total antioxidant in the lubricating composition, quantities of less than 1,000 ppm have little or minimal effectiveness whereas quantities larger than 50,000 ppm are generally not economical. Preferably the total amount of component a) and component b) in the lubricating oil composition is from about 0.1 to 2 wt % and more preferably from about 0.5 to about 2 wt % based upon the total weight of the lubricating oil composition.

Oil of Lubricating Viscosity

The lubricant compositions of this invention include a major amount of base oil of lubricating viscosity. Base Oil as used herein is defined as a base stock or blend of base stocks which is a lubricant component that is produced by a single manufacturer to the same specifications (independent of feed source or manufacturer's location): that meets the same manufacturer's specification; and that is identified by a unique formula, product identification number, or both. Base stocks may be manufactured using a variety of different processes including but not limited to distillation, solvent refining, hydrogen processing, oligomerization, esterification, and rerefining. Rerefined stock shall be substantially free from materials introduced through manufacturing, contamination, or previous use. The base oil of this invention may be any natural or synthetic lubricating base oil fraction particularly those having a kinematic viscosity at 100 degrees Centigrade (C.) and about 5 centistokes (cSt) to about 20 cSt, preferably about 7 cSt to about 16 cSt, more preferably about 9 cSt to about 15 cSt. Hydrocarbon synthetic oils may include, for example, oils prepared from the polymerization of ethylene, i.e., polyalphaolefin or PAO, or from hydrocarbon synthesis procedures using carbon monoxide and hydrogen gases such as in a Fisher-Tropsch process. A preferred base oil is one that comprises little, if any, heavy fraction; e.g., little, if any, lube oil fraction of viscosity 20 cSt or higher at 100 degrees C.

The base oil may be derived from natural lubricating oils, synthetic lubricating oils or mixtures thereof. Suitable base oil includes base stocks obtained by isomerization of synthetic wax and slack wax, as well as hydrocrackate base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Saturates levels and viscosity indices for Group I, II and III base oils are listed in Table 1. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

TABLE 1

Saturates, Sulfur and Viscosity Index of Group I, II and III Base Stocks

| Group | Saturates (As determined by ASTM D 2007) Sulfur (As determined by ASTM D 2270) | Viscosity Index (As determined by ASTM D 4294, ASTM D 4297 or ASTM D 3120) |
|---|---|---|
| I | Less than 90% saturates and/or Greater than to 0.03% sulfur | Greater than or equal to 80 and less than 120 |
| II | Greater than or equal to 90% saturates and less than or equal to 0.03% sulfur | Greater than or equal to 80 and less than 120 |
| III | Greater than or equal to 90% saturates and less than or equal to 0.03% sulfur | Greater than or equal to 120 |

Natural lubricating oils may include animal oils, vegetable oils (e.g., rapeseed oils, castor oils and lard oil), petroleum oils, mineral oils, and oils derived from coal or shale.

Synthetic oils may include hydrocarbon oils and halosubstituted hydrocarbon oils such as polymerized and interpolymerized olefins, alkylbenzenes, polyphenyls, alkylated diphenyl ethers, alkylated diphenyl sulfides, as well as their derivatives, analogues and homologues thereof, and the like. Synthetic lubricating oils also include alkylene oxide polymers, interpolymers, copolymers and derivatives thereof wherein the terminal hydroxyl groups have been modified by esterification, etherification, etc. Another suitable class of synthetic lubricating oils comprises the esters of dicarboxylic acids with a variety of alcohols. Esters useful as synthetic oils also include those made from $C_5$ to $C_{12}$ monocarboxylic acids and polyols and polyol ethers. Tri-alkyl phosphate ester oils such as those exemplified by tri-n-butyl phosphate and tri-iso-butyl phosphate are also suitable for use as base oils.

Silicon-based oils (such as the polyakyl-, polyaryl-, polyalkoxy-, or polyaryloxy-siloxane oils and silicate oils) comprise another useful class of synthetic lubricating oils. Other synthetic lubricating oils include liquid esters of phosphorus-containing acids, polymeric tetrahydrofurans, polyalphaolefins, and the like.

The base oil may be derived from unrefined, refined, rerefined oils, or mixtures thereof. Unrefined oils are obtained directly from a natural source or synthetic source (e.g., coal, shale, or tar sand bitumen) without further purification or treatment. Examples of unrefined oils include a shale oil obtained directly from a retorting operation, a petroleum oil obtained directly from distillation, or an ester oil obtained directly from an esterification process, each of which may then be used without further treatment. Refined oils are similar to the unrefined oils except that refined oils have been treated in one or more purification steps to improve one or more properties. Suitable purification techniques include distillation, hydrocracking, hydrotreating, dewaxing, solvent extraction, acid or base extraction, filtration, and percolation, all of which are known to those skilled in the art. Rerefined oils are obtained by treating used oils in processes similar to those used to obtain the refined oils. These rerefined oils are also known as reclaimed or reprocessed oils and often are additionally processed by techniques for removal of spent additives and oil breakdown products.

Base oil derived from the hydroisomerization of wax may also be used, either alone or in combination with the aforesaid natural and/or synthetic base oil. Such wax isomerate oil is produced by the hydroisomerization of natural or synthetic waxes or mixtures thereof over a hydroisomerization catalyst.

It is preferred to use a major amount of base oil in the lubricating oil of this invention. A major amount of base oil as defined herein comprises 40 wt. % or more. Preferred amounts of base oil comprise about 40 wt. % to about 97 wt. % of at least one of Group II, III and IV base oil or preferably greater than about 50 wt. % to about 97 wt. % of at least one of Group II, III and IV base oil or more preferably about 60 wt. % to about 97 wt. % of at least one of Group II, III and IV base oil. (When wt. % is used herein, it is referring to wt. % of the lubricating oil unless otherwise specified.) A more preferred embodiment of this invention may comprise an amount of base oil that comprises about 85 wt. % to about 95 wt. % of the lubricating oil.

Oil Soluble Molybdenum Compound—Component c)

Oil soluble molybdenum compounds and molybdenum/sulfur complexes are known in the art and are described, for example, in U.S. Pat. No. 4,263,152 to King et al., and U.S. Pat. No. 6,962,896 to Ruhe, the disclosures of which is hereby incorporated by reference and which are particularly preferred. Other representative of the molybdenum compounds which can be used in this invention include: glycol molybdate complexes as described by Price et al. in U.S. Pat. No. 3,285,942; overbased alkali metal and alkaline earth metal sulfonates, phenates and salicylate compositions containing molybdenum such as those disclosed and claimed by Hunt et al in U.S. Pat. No. 4,832,857; molybdenum complexes prepared by reacting a fatty oil, a diethanolamine and a molybdenum source as described by Rowan et al in U.S. Pat. No. 4,889,647; a sulfur and phosphorus-free organomolybdenum complex of organic amide, such as molybdenum containing compounds prepared from fatty acids and 2-(2-aminoethyl) aminoethanol as described by Karol in U.S. Pat. No. 5,137,647 and molybdenum containing compounds prepared from 1-(2-hydroxyethyl)-2-imidazoline substituted by a fatty residue derived from fatty oil or a fatty acid; overbased molybdenum complexes prepared from amines, diamines, alkoxylated amines, glycols and polyols as described by Gallo et al in U.S. Pat. No. 5,143,633; 2,4-heteroatom substituted-molybdena-3,3-dioxacycloalkanes as described by Karol in U.S. Pat. No. 5,412,130; and mixtures thereof. Representative molybdenum compounds of the above are commercially available and include but, are not limited to: Sakura-Lube® 700 supplied by the Asahi Denka Kogyo K.K. of Tokyo, Japan, a molybdenum amine complex; molybdenum HEX-CEM®. supplied by the OM Group, Inc., of Cleveland, Ohio, a molybdenum 2-ethylhexanoate; molybdenum octoate supplied by The Shepherd Chemical Company of Cincinnati, Ohio, a molybdenum 2-ethylhexanoate; Molyvan® 855 supplied by the R.T. Vanderbilt Company, Inc., of Norwalk, Conn., a sulfur and phosphorus-free organomolybdenum complex of organic amide; Molyvan® 856-B also from R.T. Vanderbilt, an organomolybdenum complex.

Particularly preferred oil soluble molybdenum complexes are unsulfurized or sulfurized oxymolybdenum containing compositions which can be prepared by (i) reacting an acidic molybdenum compound and a basic nitrogen compound selected from the dispersant group consisting of succinimide, a carboxylic acid amide, a hydrocarbyl monoamine, a phosphoramide, a thiophosphoramide, a Mannich base, a dispersant viscosity index improver, or a mixture thereof in the presence of a polar promoter, to form an oxymolybdenum complex. This oxymolybdenum complex can be reacted with a sulfur containing compound, to thereby form a sulfurized oxymolybdenum containing composition, useful within the context of this invention. Preferably the dispersant is a polyisobutenyl succinimide. The oxymolybdenum or sulfurized oxymolybdenum containing compositions may be generally characterized as a sulfur/molybdenum complex of a basic nitrogen dispersant compound preferably with a sulfur to molybdenum weight ratio of about (0.01 to 1.0) to 1 and more preferably from about (0.05 to 0.5) to 1 and a nitrogen to molybdenum weight ratio of about (1 to 10) to 1 and more preferably from (2 to 5) to 1. The precise molecular formula of these oxymolybdenum compositions are not known with certainty. However, they are believed to be compounds in which molybdenum, whose valences are satisfied with atoms of oxygen or sulfur, is either complexed by, or the salt of one or more nitrogen atoms of the basic nitrogen atoms of the basic nitrogen containing compound used in the preparation of these compositions. In one aspect, the oxymolybdenum complex is prepared at a reaction temperature at or below 120 degrees centigrade and if optionally sulfurized, it is also reacted at or below 120 degrees centigrade. Such a process yields a lighter color product when compared to higher temperature reaction conditions at equivalent pressure.

The molybdenum compounds used to prepare the oxymolybdenum and oxymolybdenum/sulfur complexes employed in this invention are acidic molybdenum compounds. By acidic is meant that the molybdenum compounds will react with a basic nitrogen compound as measured by ASTM test D-664 or D-2896 titration procedure. Typically these molybdenum compounds are hexavalent and are represented by the following compositions: molybdic acid, ammonium molybdate, sodium molybdate, potassium molybdate and other alkaline metal molybdates and other molybdenum salts such as hydrogen salts, e.g., hydrogen sodium molybdate, $MoOCl_4$, $MoO_2Br_2$, $Mo_2O_3Cl_6$, molybdenum trioxide, bis (acetylacetonato)-dioxomolybdenum (VI) or similar acidic molybdenum compounds. Preferred acidic molybdenum compounds are molybdic acid, ammonium molybdate, and alkali metal molybdates. Particularly preferred are molybdic acid and ammonium molybdate.

The basic nitrogen compound used to prepare the oxymolybdenum complexes have at least one basic nitrogen and are preferably oil-soluble. Typical examples of such compositions are succinimides, carboxylic acid amides, hydrocarbyl monoamines, hydrocarbon polyamines, Mannich bases, phosphoramides, thiophosphoramides, phosphonamides, dispersant viscosity index improvers, and mixtures thereof. Any of the nitrogen-containing compositions may be after-treated with, e.g., boron, using procedures well known in the art so long as the compositions continue to contain basic nitrogen. These after-treatments are particularly applicable to succinimides and Mannich base compositions.

The mono and polysuccinimides that can be used to prepare the molybdenum complexes described herein are disclosed in numerous references and are well known in the art. Certain fundamental types of succinimides and the related materials encompassed by the term of art "succinimide" are taught in U.S. Pat. Nos. 3,219,666; 3,172,892; and 3,272,746, the disclosures of which are hereby incorporated by reference. The term "succinimide" is understood in the art to include many of the amide, imide, and amidine species which may also be formed. The predominant product however is a succinimide and this term has been generally accepted as meaning the product of a reaction of an alkenyl substituted succinic acid or anhydride with a nitrogen-containing compound. Preferred succinimides, because of their commercial availability, are those succinimides prepared from a hydrocarbyl succinic anhydride, wherein the hydrocarbyl group contains from about 24 to about 350 carbon atoms, and an ethylene amine, said ethylene amines being especially characterized by ethylene diamine, diethylene triamine, triethylene tetramine, and tetraethylene pentamine. Particularly preferred are those succinimides prepared from polyisobutenyl succinic anhydride of 70 to 128 carbon atoms and tetraethylene pentamine or triethylene tetramine or mixtures thereof.

Also included within the term "succinimide" are the cooligomers of a hydrocarbyl succinic acid or anhydride and a poly secondary amine containing at least one tertiary amino nitrogen in addition to two or more secondary amino groups. Ordinarily this composition has between 1,500 and 50,000 average molecular weight. A typical compound would be that prepared by reacting polyisobutenyl succinic anhydride and ethylene dipiperazine.

Carboxylic acid amide compositions are also suitable starting materials for preparing the oxymolybdenum complexes employed in this invention. Typical of such compounds are those disclosed in U.S. Pat. No. 3,405,064, the disclosure of which is hereby incorporated by reference. These compositions are ordinarily prepared by reacting a carboxylic acid or anhydride or ester thereof, having at least 12 to about 350 aliphatic carbon atoms in the principal aliphatic chain and, if desired, having sufficient pendant aliphatic groups to render the molecule oil soluble with an amine or a hydrocarbyl polyamine, such as an ethylene amine, to give a mono or polycarboxylic acid amide. Preferred are those amides prepared from (1) a carboxylic acid of the formula R'COOH, where R' is $C_{12-20}$ alkyl or a mixture of this acid with a polyisobutenyl carboxylic acid in which the polyisobutenyl group contains from 72 to 128 carbon atoms and (2) an ethylene amine, especially triethylene tetramine or tetraethylene pentamine or mixtures thereof.

Another class of compounds which are useful in this invention are hydrocarbyl monoamines and hydrocarbyl polyamines, preferably of the type disclosed in U.S. Pat. No. 3,574,576, the disclosure of which is hereby incorporated by reference. The hydrocarbyl group, which is preferably alkyl, or olefinic having one or two sites of unsaturation, usually contains from 9 to 350, preferably from 20 to 200 carbon atoms. Particularly preferred hydrocarbyl polyamines are those which are derived, e.g., by reacting polyisobutenyl chloride and a polyalkylene polyamine, such as an ethylene amine, e.g., ethylene diamine, diethylene triamine, tetraethylene pentamine, 2-aminoethylpiperazine, 1,3-propylene diamine, 1,2-propylenediamine, and the like.

Another class of compounds useful for supplying basic nitrogen are the Mannich base compositions. These compositions are prepared from a phenol or $C_{9-200}$ alkylphenol, an aldehyde, such as formaldehyde or formaldehyde precursor such as paraformaldehyde, and an amine compound. The amine may be a mono or polyamine and typical compositions are prepared from an alkylamine, such as methylamine or an ethylene amine, such as, diethylene triamine, or tetraethylene pentamine, and the like. The phenolic material may be sulfurized and preferably is dodecylphenol or a $C_{80-100}$ alkylphenol. Typical Mannich bases which can be used in this invention are disclosed in U.S. Pat. Nos. 4,157,309 and 3,649,229; 3,368,972; and 3,539,663, the disclosures of which are hereby incorporated by reference. The last referenced patent discloses Mannich bases prepared by reacting an alkylphenol having at least 50 carbon atoms, preferably 50 to 200 carbon atoms with formaldehyde and an alkylene polyamine $HN(ANH)_nH$ where A is a saturated divalent alkyl hydrocarbon of 2 to 6 carbon atoms and n is 1-10 and where the condensation product of said alkylene polyamine may be further reacted with urea or thiourea. The utility of these Mannich bases as starting materials for preparing lubricating oil additives can often be significantly improved by treating the Mannich base using conventional techniques to introduce boron into the composition.

Another class of composition useful for preparing the oxymolybdenum complexes employed in this invention are the phosphoramides and phosphonamides such as those disclosed in U.S. Pat. Nos. 3,909,430 and 3,968,157, the disclosures of which are hereby incorporated by reference. These compositions may be prepared by forming a phosphorus compound having at least one P—N bond. They can be prepared, for example, by reacting phosphorus oxychloride with a hydrocarbyl diol in the presence of a monoamine or by reacting phosphorus oxychloride with a difunctional secondary amine and a mono-functional amine. Thiophosphoramides can be prepared by reacting an unsaturated hydrocarbon compound containing from 2 to 450 or more carbon atoms, such as polyethylene, polyisobutylene, polypropylene, ethylene, 1-hexene, 1,3-hexadiene, isobutylene, 4-methyl-1-pentene, and the like, with phosphorus pentasulfide and a nitrogen-containing compound as defined above, particularly an alkylamine, alkyldiamine, alkylpolyamine, or an alkyleneamine, such as ethylene diamine, diethylenetriamine, triethylenetetramine, tetraethylenepentamine, and the like.

Another class of nitrogen-containing compositions useful in preparing the molybdenum complexes employed in this invention includes the so-called dispersant viscosity index improvers (VI improvers). These VI improvers are commonly prepared by functionalizing a hydrocarbon polymer, especially a polymer derived from ethylene and/or propylene, optionally containing additional units derived from one or more co-monomers such as alicyclic or aliphatic olefins or diolefins. The functionalization may be carried out by a variety of processes which introduce a reactive site or sites which usually has at least one oxygen atom on the polymer. The polymer is then contacted with a nitrogen-containing source to introduce nitrogen-containing functional groups on the polymer backbone. Commonly used nitrogen sources include any basic nitrogen compound especially those nitrogen-containing compounds and compositions described herein. Preferred nitrogen sources are alkylene amines, such as ethylene amines, alkyl amines, and Mannich bases.

Preferred basic nitrogen compounds for use in this invention are succinimides, carboxylic acid amides, and Mannich bases. More preferred are succinimides having an average molecular weight of 1000 or 1300 or 2300 and mixtures thereof. Such succinimides can be post treated with boron or ethylene carbonate as known in the art.

The oxymolybdenum complexes of this invention can also be sulfurized. Representative sulfur sources for preparing the oxymolybdenum/sulfur complexes used in this invention are sulfur, hydrogen sulfide, sulfur monochloride, sulfur dichloride, phosphorus pentasulfide, $R''_2S_x$ where $R''$ is hydrocarbyl, preferably $C_{1-40}$ alkyl, and x is at least 2, inorganic sulfides and polysulfides such as $(NH_4)_2S_y$, where y is at least 1, thioacetamide, thiourea, and mercaptans of the formula $R''SH$ where $R''$ is as defined above. Also useful as sulfurizing agents are traditional sulfur-containing antioxidants such as wax sulfides and polysulfides, sulfurized olefins, sulfurized carboxylic and esters and sulfurized ester-olefins, and sulfirized alkylphenols and the metal salts thereof.

The sulfurized fatty acid esters are prepared by reacting sulfur, sulfur monochloride, and/or sulfur dichloride with an unsaturated fatty ester under elevated temperatures. Typical esters include $C_1$-$C_{20}$ alkyl esters of $C_8$-$C_{24}$ unsaturated fatty acids, such as palmitoleic, oleic, ricinoleic, petroselinic, vaccenic, linoleic, linolenic, oleostearic, licanic, paranaric, tariric, gadoleic, arachidonic, cetoleic, etc. Particularly good results have been obtained with mixed unsaturated fatty acid esters, such as are obtained from animal fats and vegetable oils, such as tall oil, linseed oil, olive oil, caster oil, peanut oil, rape oil, fish oil, sperm oil, and so forth. Exemplary fatty esters include lauryl tallate, methyl oleate, ethyl oleate, lauryl oleate, cetyl oleate, cetyl linoleate, lauryl ricinoleate, oleyl linoleate, oleyl stearate, and alkyl glycerides.

Cross-sulfurized ester olefins, such as a sulfurized mixture of $C_{10}$-$C_{25}$ olefins with fatty acid esters of $C_{10}$-$C_{25}$ fatty acids and $C_{10}$-$C_{25}$ alkyl or alkenyl alcohols, wherein the fatty acid and/or the alcohol is unsaturated may also be used.

Sulfurized olefins are prepared by the reaction of the $C_3$-$C_6$ olefin or a low-molecular-weight polyolefin derived therefrom with a sulfur-containing compound such as sulfur, sulfur monochloride, and/or sulfur dichloride.

Also useful are the aromatic and alkyl sulfides, such as dibenzyl sulfide, dixylyl sulfide, dicetyl sulfide, diparaffin wax sulfide and polysulfide, cracked wax-olefin sulfides and so forth. They can be prepared by treating the starting material, e.g., olefinically unsaturated compounds, with sulfur, sulfur monochloride, and sulfur dichloride. Particularly preferred are the paraffin wax thiomers described in U.S. Pat. No. 2,346,156.

Sulfurized alkyl phenols and the metal salts thereof include compositions such as sulfurized dodecylphenol and the calcium salts thereof. The alkyl group ordinarily contains from 9-300 carbon atoms. The metal salt may be preferably, a Group I or Group II salt, especially sodium, calcium, magnesium, or barium.

Preferred sulfur sources are sulfur, hydrogen sulfide, phosphorus pentasulfide, $R'''_2S_z$ where $R'''$ is hydrocarbyl, preferably $C_1$-$C_{10}$ alkyl, and z is at least 3, mercaptans wherein $R'''$ is $C_1$-$C_{10}$ alkyl, inorganic sulfides and polysulfides, thioacetamide, and thiourea. Most preferred sulfur sources are sulfur, hydrogen sulfide, phosphorus pentasulfide, and inorganic sulfides and polysulfides.

The polar promoter used in the preparation of the molybdenum complexes employed in this invention is one which facilitates the interaction between the acidic molybdenum compound and the basic nitrogen compound. A wide variety of such promoters are well known to those skilled in the art. Typical promoters are 1,3-propanediol, 1,4-butane-diol, diethylene glycol, butyl cellosolve, propylene glycol, 1,4-butyleneglycol, methyl carbitol, ethanolamine, diethanolamine, N-methyl-diethanol-amine, dimethyl formamide, N-methyl acetamide, dimethyl acetamide, methanol, ethylene glycol, dimethyl sulfoxide, hexamethyl phosphoramide, tetrahydrofuran and water. Preferred are water and ethylene glycol. Particularly preferred is water. While ordinarily the polar promoter is separately added to the reaction mixture, it may also be present, particularly in the case of water, as a component of non-anhydrous starting materials or as waters of hydration in the acidic molybdenum compound, such as $(NH_4)_6Mo_7O_{24}.H_2O$. Water may also be added as ammonium hydroxide.

A method for preparing the oxymolybdenum complexes used in this invention is to prepare a solution of the acidic molybdenum precursor and a polar promoter with a basic nitrogen-containing compound with or without diluent. The diluent is used, if necessary, to provide a suitable viscosity for easy stirring. Typical diluents are lubricating oil and liquid compounds containing only carbon and hydrogen. If desired, ammonium hydroxide may also be added to the reaction mixture to provide a solution of ammonium molybdate. This reaction is carried out at a variety of temperatures, typically at or below the melting point of the mixture to reflux temperature. It is ordinarily carried out at atmospheric pressure although higher or lower pressures may be used if desired. This reaction mixture may optionally be treated with a sulfur source as defined above at a suitable pressure and temperature for the sulfur source to react with the acidic molybdenum and basic nitrogen compounds. In some cases, removal of water from the reaction mixture may be desirable prior to completion of reaction with the sulfur source. In a preferred and improved method for preparing the oxymolybdenum complexes, the reactor is agitated and heated at a temperature less than or equal to about 120 degrees Celsius, preferably from about 70 degrees Celsius to about 90 degrees Celsius. Molybdic oxide or other suitable molybdenum source is then charged to the reactor and the temperature is maintained at a temperature less than or equal to about 120 degrees Celsius, preferably at about 70 degrees Celsius to about 90 degrees Celsius, until the molybdenum is sufficiently reacted. Excess water is removed from the reaction mixture. Removal methods include but are not limited to vacuum distillation or nitrogen stripping while maintaining the temperature of the reactor at a temperature less than or equal to about 120 degrees Celsius, preferably between about 70 degrees Celsius to about 90 degrees Celsius. The temperature during the stripping process is held at a temperature less than or equal to about 120 degrees Celsius to maintain the low color intensity of the molybdenum-containing composition. It is ordinarily carried out at atmospheric pressure although higher or lower pressures may be used. The stripping step is typically carried out for a period of about 0.5 to about 5 hours.

If desired, this product can be sulfurized by treating this reaction mixture with a sulfur source as defined above at a suitable pressure and temperature, not to exceed about 120 degrees Celsius for the sulfur source to react with the acidic molybdenum and basic nitrogen compounds. The sulfurization step is typically carried out for a period of from about 0.5 to about 5 hours and preferably from about 0.5 to about 2 hours. In some cases, removal of the polar promoter (water) from the reaction mixture may be desirable prior to completion of reaction with the sulfur source.

In the reaction mixture, the ratio of molybdenum compound to basic nitrogen compound is not critical; however, as the amount of molybdenum with respect to basic nitrogen increases, the filtration of the product becomes more difficult. Since the molybdenum component probably oligomerizes, it is advantageous to add as much molybdenum as can easily be maintained in the composition. Usually, the reaction mixture will have charged to it from 0.01 to 2.00 atoms of molybdenum per basic nitrogen atom. Preferably from 0.3 to 1.0, and most preferably from 0.4 to 0.7, atoms of molybdenum per atom of basic nitrogen is added to the reaction mixture.

When optionally sulfurized, the sulfurized oxymolybdenum containing compositions may be generally characterized as a sulfur/molybdenum complex of a basic nitrogen dispersant compound preferably with a sulfur to molybdenum weight ratio of about (0.01 to 1.0) to 1 and more preferably from about (0.05 to 0.5) to 1 and a nitrogen to molybdenum weight ratio of about (1 to 10) to 1 and more preferably from (2 to 5) to 1. For extremely low sulfur incorporation the sulfur to molybdenum weight ratio can be from (0.01 to 0.08) to 1.

The sulfurized and unsulfurized oxymolybdenum complexes of this invention are typically employed in a lubricating oil in an amount of 0.01 to 10%, more preferably from 0.04 to 1 wt %.

Additional components may be added to the synergist combination of component a) and component b) and optionally component c) to further the resistance to oxidation of the organic substrate and which may add to the synergism. Particularly preferred is a component which operates as a peroxy radical scavenger. These hydroperoxide decomposers convert hydroperoxides into non-radical products thus preventing chain propogation reactions. Commonly organosulfur and organophophorous compounds have severed this purpose, and many suitable compounds have identified herein above with regard the oxymolybdenum component and need not be repeated again. Particularly preferred organophosphorous compounds are the oil-soluble, phosphorus-containing, antiwear compounds selected from the group consisting of metal dithiophosphates, phosphorus esters (including phosphates, phosphonates, phosphinates, phosphine oxides, phosphites, phosphonites, phosphinites, phosphines and the like), amine phosphates and amine phosphinates, sulfur-containing phosphorus esters including phosphoro monothionate and phosphoro dithionates, phosphoramides, phosphonamides and the like. More preferably, the phosphorus-containing compound is a metal dithiophosphate and, even more preferably, a zinc dithiophosphate. Suitable phosphorous compounds are disclosed in U.S. Pat. No. 6,696,393, incorporated herein by reference.

The following additive components are examples of components that can be favorably employed in combination with the lubricating additive of the present invention. These examples of additives are provided to illustrate the present invention, but they are not intended to limit it.

(A) Ashless dispersants: alkenyl succinimides, alkenyl succinimides modified with other organic compounds such as ethylene carbonate, polysuccinimides, and alkenyl succinimides modified with boric acid, alkenyl succinic ester.

(B) Oxidation inhibitors:

1) Phenol type phenolic) oxidation inhibitors: 4,4'-methylenebis(2,6-di-tert-butylphenol), 4,4'-bis(2,6-di-tert-butylphenol), 4,4'-bis(2-methyl-6-tert-butylphenol), 2,2'-(methylenebis(4-methyl-6-tert-butyl-phenol), 4,4'-butylidenebis(3-methyl-6-tert-butylphenol), 4,4'-isopropylidenebis(2,6-di-tert-butylphenol), 2,2'-methylenebis(4-methyl-6-nonylphenol), 2,2'-isobutylidene-bis(4,6-dimethylphenol), 2,2'-methylenebis(4-methyl-6-cyclohexylphenol), 2,6-di-tert-butyl4-methylphenol, 2,6-di-tert-butyl4-ethylphenol, 2,4-dimethyl-6-tert-butyl-phenol, 2,6-di-tert-α-dimethylamino-p-cresol, 2,6-di-tert-4(N.N' dimethylaminomethylphenol), 4,4'-thiobis(2-methyl-6-tert-butylphenol), 2,2'-thiobis(4-methyl-6-tert-butylphenol), bis(3-methyl-4-hydroxy-5-tert-butylbenzyl)-sulfide, and bis (3,5-di-tert-butyl4-hydroxybenzyl).

2) Diphenylamine type oxidation inhibitor: alkylated diphenylamine, phenyl-α-naphthylamine, and alkylated α-naphthylamine.

3) Other types: metal dithiocarbamate (e.g., zinc dithiocarbamate), and methylenebis (dibutyldithiocarbamate).

(C) Rust inhibitors (Anti-rust agents):

1) Nonionic polyoxyethylene surface active agents: polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol mono-oleate, and polyethylene glycol monooleate.

2) Other compounds: stearic acid and other fatty acids, dicarboxylic acids, metal soaps, fatty acid amine salts, metal salts of heavy sulfonic acid, partial carboxylic acid ester of polyhydric alcohol, and phosphoric ester.

(D) Demulsifiers: addition product of alkylphenol and ethyleneoxide, polyoxyethylene alkyl ether, and polyoxyethylene sorbitane ester.

(E) Extreme pressure agents (EP agents): sulfurized oils, diphenyl sulfide, methyl trichlorostearate, chlorinated naphthalene, benzyl iodide, fluoroalkylpolysiloxane, and lead naphthenate.

(F) Friction modifiers: fatty alcohol, fatty acid, amine, borated ester, and other esters (G) Multifunctional additives: sulfurized oxymolybdenum dithiocarbamate, sulfurized oxymolybdenum organo phosphorodithioate, oxymolybdenum monoglyceride, oxymolybdenum diethylate amide, amine-molybdenum complex compound, and sulfur-containing molybdenum complex compound (H) Viscosity Index improvers: polymethacrylate type polymers, ethylene-propylene copolymers, styrene-isoprene copolymers, hydrated styrene-isoprene copolymers, polyisobutylene, and dispersant type viscosity index improvers.

(I) Pour point depressants: polymethyl methacrylate.

(K) Foam Inhibitors: alkyl methacrylate polymers and dimethyl silicone polymers.

(L) Wear inhibitors: zinc dialkyldithiophosphate (Zn-DTP, primary alkyl type & secondary alkyl type).

EXAMPLES

The invention is further illustrated by the following examples, which are not to be considered as limitative of its scope. A further understanding of the invention can be had in the following nonlimiting Preparations and Examples. Wherein unless expressly stated in the contraty, all temperatures and temperatures ranges refer to the Centigrade system and the term "ambient" or "room temperature" refers to about 20 to 25° C. The term "percent or %" refers to weight percent, and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r) were determined at 300 mHz, signals are assigned as singlets(s), braod singlets (bs), doublets (d), double doublets (dd), triplets (t), double triplets (dt), quartets (q), and multiplets (m), and cps refers to cycles per second.

Preparation of the benzo[b]perhydroheterocyclic aryl amine compounds which are particularly useful as a first antioxidant in the mixture of antioxidants of the composition of the present invention are illustrated herein below.

Example 1

Preparation of Phenyl-(1,2,3,4-tetrahydro-quinolin-6-yl)-amine

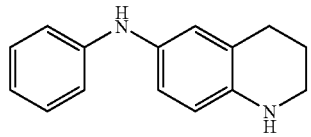

A solution of 20.4 grams of 6-anilinoquinoline (prepared as described in Buu-Hoi, Royer and Hubert-Habart, *J. Chem. Soc.*, 1956, 2048-2051) in 400 mL of acetic acid containing 1.3 grams of platinum(IV) oxide was hydrogenated at 30 psi for 4.2 hours on a Parr low-pressure hydrogenator. The solution was filtered; and the filtrate was neutralized with 6N aqueous sodium hydroxide. The aqueous phase was extracted three times with dichloromethane. The combined dichloromethane layers were washed with 6N aqueous sodium hydroxide followed by brine. The dichloromethane layer was dried over anhydrous magnesium sulfate, filtered and concentrated in vacuo to yield 20.4 grams of a dark residue. The dark residue was recrystallized from 95% ethanol to yield 15.2 grams of the desired product as a grey solid. $^1$H NMR (CDCl$_3$) δ 7.2 (m, 2H), 6.8 (m, 4H), 6.45 (d, 1H), 5.35 (bs, 1H), 3.4 (bs, 1H), 3.25 (t, 2H), 2.75 (t, 2H), 1.95 (p, 2H).

Example 2

Preparation of N-(4-tert-butylphenyl)-1,2,3,4-tetrahydroquinolin-8-amine

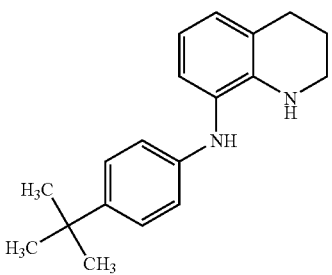

To a flask equipped with a magnetic stirrer, reflux condenser, and nitrogen inlet was added 8-aminoquinoline (14.4 grams, 0.10 moles), 4-tert-butyl bromobenzene (21.3 grams, 0.10 moles), tris(dibenzylideneacetone)dipalladium (0) (1.8 grams, 0.002 moles), rac-2,2'-bis(diphenylphosphino)-1,1'-binapthyl (2.5 grams, 0.004 moles), sodium tert-butoxide (19.4 grams, 0.20 moles) and anhydrous toluene (150 mL). The contents of the flask were refluxed for four days; cooled to room temperature; and filtered through a pad of silica gel. The silica gel pad was then eluted with dichloromethane (240 mL). The combined organic layers were concentrated in vacuo to yield a dark blue solid. The solid was chromatographed on silica gel, eluting with hexane/ethyl acetate (20:1) to afford 23 grams of the desired product as a yellow solid. $^1$H NMR (CDCl$_3$) δ 8.8 (m, 1H), 8.2 (bs, 1H), 8.1 (d, 1H), 7.1-7.5 (m, 9H), 1.35 (s, 9H).

A solution of 2.46 grams of N-(4-tert-butylphenyl)quinolin-8-amine prepared above in 100 mL of acetic acid containing 0.15 grams of platinum(IV) oxide was hydrogenated at 45 psi for 1.5 hours on a Parr low-pressure hydrogenator. The solution was filtered through diatomaceous earth; concentrated in vacuo; and neutralized with 3N aqueous sodium hydroxide. The aqueous phase was diluted with water and extracted three times with ethyl acetate. The combined ethyl acetate layers were washed with brine; dried over anhydrous magnesium sulfate, filtered and concentrated in vacuo to yield 2.5 grams of dark blue oil. The oil was chromatographed on silica gel, eluting with hexane/ethyl acetate (20:1) to afford 2.0 grams of the desired product as a yellow oil. $^1$H NMR (CDCl$_3$) δ 7.2 (d, 2H), 6.5-6.95 (m, 5H), 4.95 (bs, 1H), 3.3 (t, 2H), 2.8 (t, 2H), 1.9 (p, 2H), 1.3 (s, 9H).

Example 3

Preparation of N-2-naphthyl-1,2,3,4-tetrahydroquinolin-6-amine

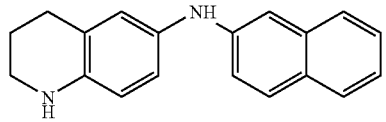

To a flask equipped with a magnetic stirrer, reflux condensor, and nitrogen inlet was added 6-aminoquinoline (6.69 grams, 46.4 mmoles), 2-bromonapthalene (9.15 grams, 44.2 mmoles), tris(dibenzylideneacetone)dipalladium (0) (0.80 grams, 0.87 mmoles), rac-2,2'-bis(diphenylphosphino)-1,1'-binapthyl (1.10 grams, 1.77 mmoles), sodium tert-butoxide (8.49 grams, 88.3 mmoles) and anhydrous toluene (90 mL). The contents of the flask were refluxed for five hours; cooled to room temperature; and filtered through a pad of silica gel. The silica gel pad was then eluted with tetrahydrofuran (135 mL). The combined organic layers were concentrated in vacuo to yield a brown solid. The solid was recrystallized from ethanol to afford 8.6 grams of the desired product as a yellow solid. $^1$H NMR (DMSO-d$_6$/D$_2$O) δ 8.9 (d, 1H), 8.65 (d, 1H), 8.2 (d, 1H), 7.25-8.05 (m, 10H).

A solution of 7.00 grams of N-2-naphthylquinolin-6-amine from above in acetic acid (60 mL) and ethyl acetate (10 mL) containing 0.55 grams of platinum(IV) oxide was hydrogenated at 45 psi for 6.0 hours on a Parr low-pressure hydrogenator. The solution was filtered through diatomaceous earth; concentrated in vacuo; and neutralized with 3N aqueous sodium hydroxide. The aqueous phase was diluted with water and extracted three times with ethyl acetate. The combined ethyl acetate layers were washed with brine; dried over anhydrous magnesium sulfate, filtered and concentrated in vacuo to yield 5.5 grams solid. The solid was chromatographed on silica gel, eluting with hexane/ethyl acetate gradient to afford 3.5 grams of the desired product as a yellow solid. $^1$H NMR (CDCl$_3$/D$_2$O) δ 6.4-7.8 (m, 10H), 3.1-3.5 (m, 2H), 2.6-2.9 (m, 2H), 1.95 (p, 2H).

Example 4

Preparation of N-2-naphthyl-1,2,3,4-tetrahydroquinolin-8-amine

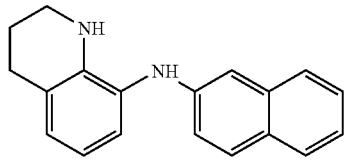

To a flask equipped with a magnetic stirrer, reflux condensor, and nitrogen inlet was added 8-aminoquinoline (6.81 grams, 47.2 mmoles), 2-bromonapthalene (9.58 grams, 46.3 mmoles), tris(dibenzylideneacetone)dipalladium (0) (0.84 grams, 0.92 mmoles), rac-2,2'-bis(diphenylphosphino)-1,1'-binapthyl (0.6 grams, 0.92 mmoles), sodium tert-butoxide (8.86 grams, 92.2 mmoles) and anhydrous toluene (90 mL). The contents of the flask were refluxed for sixteen hours; cooled to room temperature; and filtered through a pad of silica gel. The silica gel pad was then eluted with dichloromethane (135 mL). The combined organic layers were concentrated in vacuo to yield a yellow solid. The solid was chromatographed on silica gel, eluting with a hexane/ethyl acetate gradient to afford 6.6 grams of the desired product as a yellow solid. $^1$H NMR (CDCl$_3$) δ 8.75 (d, 1H), 8.4 (bs, 1H), 8.05 (d, 1H), 7.6-7.9 (m, 5H), 7.25-7.5 (m,5H), 7.2 (d, 1H).

A solution of 4.08 grams of N-2-naphthylquinolin-8-amine from above in acetic acid (10 mL) and ethyl acetate (150 mL) containing 0.24 grams of platinum(IV) oxide was hydrogenated at 45 psi for four hours on a Parr low-pressure hydrogenator. The solution was filtered through diatomaceous earth; concentrated in vacuo; and neutralized with 3N aqueous sodium hydroxide. The aqueous phase was diluted with water and extracted three times with ethyl acetate. The combined ethyl acetate layers were washed with brine; dried over anhydrous magnesium sulfate, filtered and concentrated in vacuo to yield 4.2 grams of the desired product as a purple oil. $^1$H NMR (CDCl$_3$/D$_2$O) δ 7.7 (m, 2H), 7.6 (d,1H), 7.35 (t, 1H), 7.25 (m, 1H), 7.05 (m, 2H), 6.9 (m, 2H), 6.6 (t, 1H), 3.3 (t, 2H), 2.85 (t, 2H), 1.95 (p, 2H).

Example 5

Preparation of N-(4-tert-butylphenyl)-2,3-dihydro-1-benzofuran-5-amine

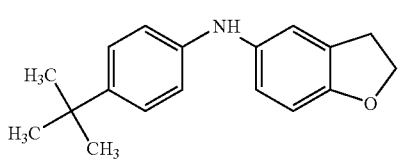

To a flask equipped with a magnetic stirrer, reflux condensor, and nitrogen inlet was added 2,3-dihydro-1-benzofuran-5-amine (11.6 grams, 85.8 mmoles, prepared as in Example 23 of U.S. Pat. No. 20040029932), 4-tert-butyl bromobenzene (18.1 grams, 85 mmoles), tris(dibenzylideneacetone) dipalladium (0) (1.6 grams, 1.7 mmoles), rac-2,2'-bis(diphenylphosphino)-1,1'-binapthyl (2.1 grams, 3.4 mmoles), sodium tert-butoxide (16.4 grams, 0.17 moles) and anhydrous toluene (100 mL). The contents of the flask were refluxed for three days; cooled to room temperature; and filtered through a pad of silica gel. The silica gel pad was then eluted with dichloromethane (150 mL). The combined organic layers were concentrated in vacuo to yield a dark solid. The solid was chromatographed on silica gel, eluting with hexane/ethyl acetate (20:1) to afford 10 grams of the desired product as a white solid. $^1$H NMR (CDCl$_3$) δ 7.25 (d, 2H), 6.95 (s, 1H), 6.85 (d, 3H), 6.7 (d, 1H), 5.4 (bs, 1H), 4.5 (t, 2H), 3.15 (t, 2H), 1.3 (s, 9H).

Example 6

Preparation of N'-(2,3-dihydro-1-benzofuran-5-yl)-N,N-diethylbenzene-1,4-diamine

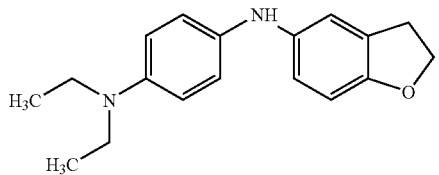

To a flask equipped with a magnetic stirrer, reflux condensor, and nitrogen inlet was added N,N-diethyl-1,4-phenylenediamine (3.35 grams, 20.4 mmoles), 5-bromo-2,3-dihydrobenzofuran (3.4 grams, 17.1 mmoles), tris (dibenzylideneacetone)dipalladium (0) (0.39 grams, 0.43 mmoles), rac-2,2'-bis(diphenylphosphino)-1,1'-binapthyl (2.1 grams, 3.4 mmoles), sodium tert-butoxide (0.71 grams, 1.28 mmoles) and anhydrous toluene (90 mL). The contents of the flask were heated to 80° C. for two days; cooled to room temperature; and filtered through a pad of silica gel. The silica gel pad was then eluted with dichloromethane (200 mL). The combined organic layers were concentrated in vacuo to yield a dark blue oil. The oil was chromatographed on silica gel, eluting with a hexane/ethyl acetate gradient to afford 4.2 grams of the desired product as a brown oil. $^1$H NMR (CDCl$_3$) δ 6.6-7.0 (m, 7H), 5.15 (bs, 1H), 4.5 (t, 2H), 3.05-3.2 (m, 6H), 1.1 (t, 6H).

Example 7

Preparation of N-(4-tert-butylphenyl)-2,3-dihydro-1,4-benzodioxin-6-amine

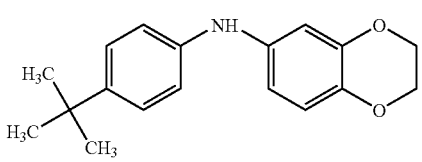

To a flask equipped with a magnetic stirrer, reflux condenser, and nitrogen inlet was added 1,4-benzodioxin-6-amine (5.26 grams, 34.8 mmoles), 4-tert-butyl bromobenzene (6.83 grams, 32.1 mmoles), tris(dibenzylideneacetone) dipalladium (0) (0.58 grams, 0.6 mmoles), rac-2,2'-bis (diphenylphosphino)-1,1'-binapthyl (0.79 grams, 1.2 mmoles), sodium tert-butoxide (6.08 grams, 63.0 mmoles) and anhydrous toluene (70 mL). The contents of the flask were refluxed for three days; cooled to room temperature; and filtered through a pad of silica gel. The silica gel pad was then eluted with dichloromethane (300 mL). The combined organic layers were concentrated in vacuo to yield a dark solid. The solid was chromatographed on silica gel, eluting with a hexane/ethyl acetate gradient to afford 5 grams of the desired product as a white solid. $^1$H NMR (CDCl$_3$) δ 7.25 (d, 2H), 6.9 (d, 2H), 6.75 (d, 1H), 6.5-6.7 (m, 2H), 5.4 (bs, 1H), 4.2 (s, 4H), 1.3 (s, 9H).

Example 8

Preparation of N-(4-butylphenyl)-1,2,3,4-tetrahydro-quinolin-8-amine

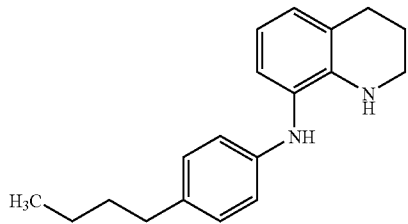

To a flask equipped with a magnetic stirrer, reflux condenser, and nitrogen inlet was added 8-hydroxyquinoline (20.0 grams, 0.14 moles), 4-butyl aniline (24.0 grams, 0.16 moles) and iodine (0.52 grams, 2.0 mmoles). The contents of the flask were refluxed for eight days; cooled to room temperature; and diluted with toluene. The toluene solution was filtered through diatomaceous earth and further diluted with dichloromethane. The solution was washed with 5% aqueous sodium hydroxide three times and water three times. The organic layer was dried over magnesium sulfate, filtered and concentrated in vacuo to yield a dark brown oil. The oil was chromatographed on silica gel, eluting with hexane/ethyl acetate (10:1) to afford 3.7 grams a brown oil.

The oil in 70 mL of acetic acid containing 0.22 grams of platinum (IV) oxide was hydrogenated at 35 psi for 4.5 hours on a Parr low-pressure hydrogenator. The solution was filtered; and the filtrate was neutralized with 6N aqueous sodium hydroxide. The aqueous phase was extracted three times with dichloromethane. The combined dichloromethane layers were washed with 6N aqueous sodium hydroxide followed by brine. The dichloromethane layer was dried over anhydrous magnesium sulfate, filtered and concentrated in vacuo to yield 3.9 grams of a dark brown oil. The oil was chromatographed on silica gel, eluting with a hexane/ethyl acetate gradient to afford 2.1 grams of the desired product as a yellow oil $^1$H NMR (CDCl$_3$) δ 7.05 (d, 2H), 6.95 (d, 1H), 6.80 (d, 1H), 6.70 (d, 2H), 6.6 (t, 1H), 4.95 (bs, 1H), 4.05 (bs, 1H), 3.3 (t, 2H), 2.8 (t, 2H), 2.5 (t, 2H), 1.95 (p, 2H), 1.55 (p, 2H), 1.35 (h, 2H), 0.95 (t, 3H).

PERFORMANCE EXAMPLES

Oxidation studies of the products of selected Examples were carried out in a bulk oil oxidation bench test as described by E. S. Yamaguchi et al. in Tribology Transactions, Vol. 42(4), 895-901 (1999). In this test the rate of oxygen uptake at constant pressure by a given weight of oil was monitored. The time required (induction time) for rapid oxygen uptake per 25 grams of sample was measured at 171° C. under 1.0 atmosphere of oxygen pressure. The sample was stirred at 1000 revolutions per minute. The results are reported, however, as time for rapid oxygen uptake per 100 grams of sample. The oil contained a catalyst added as oil soluble naphthenates to provide 26 ppm iron, 45 ppm copper, 512 ppm lead, 2.3 ppm manganese, and 24 ppm tin.

Performance Examples 1-8

A base line formulation was prepared which to asses the performance of the mixture of: component a) a benzo[b] perhydrohetercyclic arylamine of formula I; and component b) a diarylamine, in the oxidator bench test. The base line formulation—Formulation A, contained in a Group 2+ base oil, 12.5 mmoles/kg dialkyl zinc dithiophosphate, 5.0% polyisobutenyl succinimide, 35.0 mmoles/kg overbased calcium sulfonate detergent, 15.0 mmole/kg calcium phenate detergent and 0.3% V.I. improver. The Formulation A baseline was tested in the bulk oil oxidation bench test above and resulted in a value of 11.5 hours to rapid O$_2$ uptake. To this baseline (Formulation A) were added varying amounts of component a) and component b) but, keeping the total addition of component a) and component b) constant at 1 weight percent.

Performance Example 1, illustrates improvement in the oxidative stability of the top treated Formulation A by the addition of a 1 wt % of a commercially available alkylated diphenylamine (mixture t-butyl and t-octyl—prepared by alkylating diphenylamine with 2,4,4-trimethylpentene) and sold by Ciba-Geigy as Irganox® L-57. Similiarly, Performance Example 8, illustrates improvement in the oxidative stability of the top treated Formulation A by the addition of a 1 wt % of a compound prepared according to Example 1 above, namely a phenyl-(1,2,3,4-tetrahydro-quinolin-6-yl)-amine. The oxidation study results are shown in Table 1. Surprisingly, the results are not merely additive of the contribution of each component, but show a dramatic improvement by the combination of component a) and component b). The addition of a small amount of component a) to component b) can yield results better that either component alone, for example see Performance Examples 4-7. For example, if they merely additive then the calculated contribution of each component in Performance Example 6 would be=(0.75*54.0+0.25*33.0) or 48.75 (calculated) as opposed to the actual performance of 70.0. This improvement is quite unexpected. Oxidation bench test results are presented in Table 1.

TABLE 1

| | Synergistic Mixture Top Treated to Formulation A | | |
|---|---|---|---|
| Performance Example | Component a) Example 1 concentration (weight percent) | Component b) Alkylated diphenylamine[1] concentration (weight percent) | Results Hr to rapid O$_2$ uptake |
| 1 | 0 | 1 | 33.0 |
| 2 | 0.15 | 0.85 | 38.0 |
| 3 | 0.3 | 0.7 | 47.0 |
| 4 | 0.45 | 0.55 | 55.0 |
| 5 | 0.6 | 0.4 | 60.0 |
| 6 | 0.75 | 0.25 | 70.0 |
| 7 | 0.9 | 0.1 | 60.0 |
| 8 | 1.0 | 0 | 54.0 |

[1]Irganox ® L57 is available commercially from Ciba-Geigy

Performance Examples 9-16

A second base line formulation was prepared which to asses the performance of the mixture of: component a) a benzo[b]perhydrohetercyclic arylamine of formula I; and component b) a diarylamine, in the oxidator bench test. Component b) in these examples is the same component b) as was used above. Formulation B contained in a Group 2+ base oil 7.0 mmoles/kg dialkyl zinc dithiophosphate, 4.0% polyisobutenyl succinimide, 0.5% polyisobutenyl succinimide (this polyisobutenyl succinimide also contains 5.5 weight percent molybdenum), 48.5 mmoles/kg overbased calcium sulfonate detergent and 0.3% V.I. improver. Similarly to above, Performance Examples 9 and 16 in Table 2, illustrate the contribution of components b) and component a) respectively. As illustrated in Table 2, the addition of a small amount of component a) to component b) can yield results better that either component alone, for example see Performance Examples 11-15.

TABLE 2

Synergistic Mixture Top Treated to Formulation B

| Performance Example | Component a) Example 1 concentration (weight percent) | Component b) Alkylated diphenylamine concentration (weight percent) | Results Hr to rapid $O_2$ uptake |
|---|---|---|---|
| 9  | 0    | 1    | 38.0  |
| 10 | 0.15 | 0.85 | 58.0  |
| 11 | 0.3  | 0.7  | 71.5  |
| 12 | 0.45 | 0.55 | 82.0  |
| 13 | 0.6  | 0.4  | 95.0  |
| 14 | 0.75 | 0.25 | 100.0 |
| 15 | 0.9  | 0.1  | 95.0  |
| 16 | 1.0  | 0    | 71.5  |

The data from Table 2 is graphically presented in FIG. 1. In this graph, the mixture of component a) and component b) is plotted against the results of the oxidation test, referred to on the figure as Oxidator BX. The calculated additive contribution of the components is displayed as the linearly on FIG. 1. As graphically illustrated the combination of component a) and component b) is much greater than would be expected if the contributions were merely additive.

Tables 1 and 2 demonstrate a synergy between the combination of component a) component b) which is greater than the additive contribution of each component; and quite surprisingly, as illustrated for ratios from about 0.45/0.55 to about 0.9/0.1 is mixture has performance better than either component alone. Moreover, in comparison of the overall data of Table 1 and Table 2, it is evident the addition of an oil soluble molybdenum compound can further lead to dramatic improvement in the oxidative stability of the formulation.

Performance Examples 17-24

A third base line formulation was prepared to assess the performance of the mixture of: component a) a 0.375 weight percent of benzo[b]perhydrohetercyclic arylamine of formula I; and component b) a 0.125 weight percent diarylamine, in the oxidator bench test with varying amounts of component c) a molybdenum containing polyisobutenyl succinimide prepared as described in U.S. Pat. No. 6,962,896 to Ruhe (this polyisobutenyl succinimide contains 5.5 weight percent molybdenum). Components a) and b) in these examples is the same components a) and b) as was used above. Formulation C contained in a Group 2+ base oil 7.0 mmoles/kg dialkyl zinc dithiophosphate, 4.0% polyisobutenyl succinimide, 48.5 mmoles/kg overbased calcium sulfonate detergent, 0.3% V.I. improver, 0.375% phenyl-(1,2,3,4-tetrahydro-quinoline-6-yl)-amine and 0.125% Irganox® L57. Performance Examples 17 to 24 in Table 3, as well as comparison of the overall data of Table 1 and Table 2 illustrates that the addition of component c) to the combination of components a) and component b) enhances their perfomance.

TABLE 3

| Performance Example | Component c) concentration (weight percent) | Results Hr to rapid $O_2$ uptake |
|---|---|---|
| 17 | 0     | 26.0 |
| 18 | 0.125 | 31.0 |
| 19 | 0.250 | 34.5 |
| 20 | 0.500 | 42.0 |
| 21 | 0.750 | 48.0 |
| 22 | 1.000 | 55.5 |
| 23 | 1.500 | 55.0 |
| 24 | 2.000 | 47.5 |

What is claimed is:

1. A composition comprising a lubricating oil and a synergistic mixture of antioxidants, said mixture comprising a) from 0.1 to 10 weight percent of a first antioxidant according to formula I:

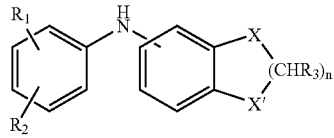

Formula I wherein $R_1$ and $R_2$ are each independently selected from the group consisting of hydrogen, alkyl from 1 to 20 carbon atoms, —OR, —SR and —NRR', where R and R' are independently hydrogen or alkyl from 1 to 6 carbon atoms, or $R_1$ and $R_2$ when adjacent to each other together form a 5 to 6 membered alicyclic or aromatic ring which may be optionally substituted with 1 or 2 alkyl groups each having from 1 to 20 carbon atoms;

each $R_3$ is hydrogen or alkyl from 1 to 6 carbon atoms,

X and X' are independently selected from —$CHR_4$—, oxygen, sulfur or $NR_5$, wherein $R_4$ and $R_5$ are independently hydrogen or alkyl from 1 to 6 carbon atoms, with the proviso that at least one of X or X' is a heteroatom positioned ortho or para to the bridging nitrogen atom, and when X or X' are nitrogen then $R_1$ or $R_2$ is not hydroxyl; and further provided that when one of X or X' is —$CHR_4$— then the other may not be oxygen; and n is an integer from 1 to 2; and b) from 0.01 to 10 weight percent of a second antioxidant selected from the formula

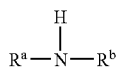

wherein $R^a$ and $R^b$ are each independently aryl from 6 to 10 carbon atoms which may be unsubstituted or substituted with one or two alkyl groups each having from 1 to 20 carbon atoms.

2. The composition according to claim 1, wherein the ratio of component a) to component b) is from about 0.5:1 to about 10:1.

3. The composition according to claim 2, wherein the ratio of component a) to component b) is from about 0.75:1 to about 5:1.

4. The composition according to claim 2, wherein the total weight percent of the mixture of antioxidants in the composition is less than 5 weight percent.

5. The composition according to claim 1, wherein in component a): at least one X and X' are selected from $NR_5$ and oxygen.

6. The composition according to claim 5, wherein in component a): at least one X and X' is $NR_5$.

7. The composition according to claim 6, wherein in component a): X is —$CHR_4$— and X' is $NR_5$.

8. The composition according to claim 7, wherein in component a): n is 2.

9. The compound according to claim 8, wherein in component a): $R_3$, $R_4$ and $R_5$ are each hydrogen.

10. The composition according to claim 7, wherein in component a): $R_1$ and $R_2$ are each independently selected from the group consisting of hydrogen, alkyl from 1 to 20 carbon atoms, or $R_1$ and $R_2$ when adjacent to each other together form a 5 to 6 membered alicyclic or aromatic ring which may be optionally substituted with 1 or 2 alkyl groups each having from 1 to 20 carbon atoms.

11. The composition according to claim 10, wherein in component a): $R_1$ and $R_2$ are each independently selected from the group consisting of hydrogen and alkyl from 1 to 20 carbon atoms.

12. The composition according to claim 5, wherein in component a): at least one X and X' is sulfur.

13. The composition according to claim 5, wherein in component a): X and X' are independently selected from oxygen, sulfur or $NR_5$, wherein $R_5$ is hydrogen or alkyl from 1 to 6 carbon atoms.

14. The composition according of claim 13, wherein in component a): X and X' are oxygen.

15. The composition according to claim 1, wherein in component a): $R_1$ and $R_2$ are adjacent to each other and together form a 5 to 6 membered aromatic ring which may be optionally substituted with 1 or 2 alkyl groups each having from 1 to 6 carbon atoms.

16. The composition according to claim 1, wherein in component a): $R_1$ is hydrogen and $R_2$ is selected from the group consisting of alkyl from 1 to 20 carbon atoms, —OR, —SR and —NRR', where R and R' are independently hydrogen or alkyl from 1 to 6 carbon atoms.

17. The composition according to claim 16, wherein in component a): $R_2$ is —NRR' where R and R' are alkyl from 1 to 6.

18. The composition according to claim 1, wherein component b) is selected from the group consisting of diphenylamine, monoalkylated diphenylamine, dialkylated diphenylamine, trialkylated diphenylamine, and mixtures thereof.

19. The composition according to claim 18, wherein component b) is selected from the group consisting of butyldiphenylamine, di-butyldiphenylamine, octyldiphenylamine, di-octyldiphenylamine, nonyldiphenylamine, di-nonyldiphenylamine, t-butyl-t-octyldiphenylamine, and mixtures thereof.

20. The composition according to claim 18, wherein component b) is selected from the group consisting of phenyl-alpha-naphthylamine, phenyl-beta-naphthylamine, t-octylated N-phenyl-1-naphthylamine.

21. The composition according to claim 1, further comprising component c) an oil soluble molybdenum compound.

22. The composition according to claim 21, wherein component c) is an unsulfurized or sulfurized oxymolybdenum containing composition prepared by (i) reacting an acidic molybdenum compound and a basic nitrogen compound selected from the dispersant group consisting of succinimide, a carboxylic acid amide, a hydrocarbyl monoamine, a phosphoramide, a thiophosphoramide, a Mannich base, a dispersant viscosity index improver, or a mixture thereof in the presence of a polar promoter, to form an oxymolybdenum complex.

23. The composition according to claim 22, wherein the basic nitrogen is a succinimide.

24. The composition according to claim 1, further comprising an oil-soluble, phosphorus-containing, anti-wear compound selected from the group consisting of metal dithiophosphates, phosphorus esters, amine phosphates and amine phosphinates, sulfur-containing phosphorus esters, phosphoramides and phosphonamides.

25. The composition according to claim 24, wherein said phosphorus esters are selected from the group consisting of phosphates, phosphonates, phosphinates, phosphine oxides, phosphites, phosphonites, phosphinites, and phosphines.

26. The composition according to claim 24, wherein the oil-soluble, phosphorus-containing, anti-wear compound is a metal dithiophosphate.

27. The composition according to claim 26, wherein the metal dithiophosphate is a zinc dialkyldithiophosphate.

* * * * *